United States Patent [19]

Shulman

[11] Patent Number: 4,599,354
[45] Date of Patent: Jul. 8, 1986

[54] COMPOSITION AND METHOD FOR PRODUCING PROLONGED PAIN RELIEF

[76] Inventor: Morton Shulman, 1115 Thorntree La., Highland Park, Ill. 60035

[21] Appl. No.: 710,416

[22] Filed: Mar. 11, 1985

[51] Int. Cl.⁴ .................. A61K 31/24; A61K 31/215; A61K 31/745
[52] U.S. Cl. .................................... 514/530; 424/83; 514/535
[58] Field of Search ................... 424/83; 514/535, 530

[56] References Cited

U.S. PATENT DOCUMENTS 4,344,965 8/1982 Stone .................................. 514/535

OTHER PUBLICATIONS

The Pharmacological Basics of Therapeutics, Louis S. Goodman et al., The MacMillan Company, New York, 1955, p. 370.
Neural Blockade In Clinical Anesthesia and Management of Pain, edited by Michael J. Cousins et al, J. B. Lippincott Company, Philadelphia, 1980, p. 102.
Kenny, "Relief of Pain In Intractable Cancer of The Pelvis", British Medical Journal, Nov. 29, 1947, p. 862.
Teevens, "Relief of Sciatica In Carcinoma of The Prostate by Protocaine", Canad. M. A.J., Apr. 1948, vol. 58, p. 384.
Swerdlow, "Relief of Intractable Pain, Monographs in Anaesthesiology", vol. 1, Excerpta Medica, Amsterdam, London, New York, 1974, p. 169.
Katz et al, "Neuropathology of Neurolytic and Semidestructive Agents," in Neural Blockade in Clinical Anesthesia and Management of Pain, edited by Michael J. Cousins et al, J.B. Lipincott Company, Philadelphia, 1980, p. 128.

*Primary Examiner*—Stanley J. Friedman
*Attorney, Agent, or Firm*—Marshall, O'Toole, Gerstein, Murray & Bicknell

[57] ABSTRACT

A composition and method for producing lasting pain relief in a body by injection. The composition consists essentially of a sterile, stable suspension of butyl aminobenzoate in a non-toxic, aqueous carrying medium in which the butyl aminobenzoate is insoluble. The composition is substantially devoid of dextran and contains polyethylene glycol as a suspending agent.

22 Claims, No Drawings

COMPOSITION AND METHOD FOR PRODUCING PROLONGED PAIN RELIEF

BACKGROUND OF THE INVENTION

The present invention relates generally to compositions and methods for producing prolonged pain relief and more particularly to injectable local anesthetics for that purpose.

Intractable pain, such as that suffered by cancer patients or patients with back problems, is a serious clinical problem in that it oftentimes does not respond to conventional modes of therapy. Some modes of treatment, although relieving pain, produce undesirable side effects. An example thereof is the use of epidural phenol injections to treat intractable cancer pain. This method is usually effective, but it oftentimes produces motor weakness and loss of bowel and bladder control as possible complications.

There is a group of local anesthetic compounds, comprising ethyl aminobenzoate (benzocaine) and butyl aminobenzoate (butamben), characterized by the fact that its members are poorly soluble in water. Due to this insolubility, the compounds are not absorbed with sufficient rapidity to be toxic and therefore can be applied directly to surface wounds and ulcerated surfaces. For the same reason, these compounds remain localized at the site of application for long periods of time, producing a sustained anesthetic action.

The aforementioned water-insoluble, local anesthetics are soluble in non-aqueous media such as oils or glycerol, but solutions of this type cannot be injected because of severe nerve damage that can result from such a solvent.

There is a book entitled "Neural Blockage In Clinical Anesthesia And Management Of Pain", edited by Michael J. Cousins et al, J. B. Lippincott Company, Philadelphia, 1980. Chapter 4 therein by Scott and Cousins is entitled "Clinical Pharmacology of Local Anesthetic Agents", and at page 102 it discloses the use of benzocaine as an injectable local anesthetic, either dissolved in urethane or suspended in dextran, the latter being preferable as a carrier because urethane is now known to be carcinogenic. Because of its relative insolubility in water, injected benzocaine (2% dissolved in urethane) reportedly remains at the injection site for a time which provides a nerve block that lasts many hours or even days.

Water-soluble local anesthetics are of limited pain relieving duration, relief being no more than a matter of hours.

Polyethylene glycol has been used as a suspending agent for steroids when the latter have been injected as an anti-inflammatory agent.

SUMMARY OF THE INVENTION

Butyl aminobenzoate is more insoluble in water than is the related local anesthetic, benzocaine. Thus, in accordance with the present invention, butyl aminobenzoate should be of longer lasting duration as a local anesthetic than is benzocaine.

However, when butyl aminobenzoate is mixed with up to 1% dextran (the recommended suspending agent for benzocaine) the result is an amorphous mass which settles out of suspension when stirring is stopped, and it is not suitable for injection. In accordance with the present invention, it has been determined that butyl aminobenzoate can be stably suspended with other non-toxic suspending agents, e.g. polyethylene glycol, in an aqueous carrying medium, but dextran must be excluded from the carrying medium, notwithstanding the fact that dextran is the recommended suspending agent for benzocaine, a related local anesthetic. Dextran impairs or destroys the ability of polyethylene glycol to function as a suspending agent for butyl aminobenzoate.

The essence of the present invention is a composition for producing long lasting pain relief in a body region by injection. The composition consists essentially of a sterile, stable suspension of butyl aminobenzoate in a non-toxic, aqueous carrying medium in which butyl aminobenzoate is insoluble. The suspension is substantially devoid of dextran.

A composition in accordance with the present invention has been used to treat intractable pain in patients who obtained no relief from conventional modes of treatment. When treated in accordance with the present invention, the patients obtained long lasting relief having a duration of weeks or months.

Other features and advantages are inherent in the composition and method claimed and disclosed or will become apparent to those skilled in the art from the following detailed description.

DETAILED DESCRIPTION

In accordance with the present invention, there is provided a composition for producing lasting pain relief in a body region by injection. This composition consists essentially of a sterile, stable suspension of butyl aminobenzoate in a non-toxic aqueous carrying medium in which the butyl aminobenzoate is insoluble. The aqueous carrying medium consists essentially of a high molecular weight, water soluble suspension agent for butyl aminobenzoate, and water.

The suspension agent has a molecular weight of at least about 1000. A typical suspension agent is polyethylene glycol having a molecular weight in the range of 1000–5000. The polyethylene glycol is typically present in an amount up to about 10 wt. %, based on the total weight of the polyethylene glycol and water in the aqueous carrying medium.

The aqueous carrying medium may also contain sufficient sodium chloride to make an isotonic solution having the same osmololity (solute concentration) as extracellular body fluid. In addition, the aqueous carrying medium contains sufficient inorganic acid (e.g. hydrochloric acid) to provide the liquid carrying medium with a pH in the range of 3 to 5 (e.g. 4). A pH in this range makes the suspension more stable during subsequent sterilization, e.g. by autoclaving, than a suspension having a higher pH. The pH should be sufficiently low to produce the desired stability but not so low (acidic) as to cause tissue damage when the composition is injected into the body.

The liquid carrying medium is substantially devoid of dextran as this has an adverse affect on the suspension of butyl aminobenzoate in the liquid carrying medium. Dextran impairs or destroys the ability of polyethylene glycol to act as a suspending agent for butyl aminobenzoate and renders the composition unsuitable for injection.

The butyl aminobenzoate constitutes about 5 to 15 wt. % of the composition (e.g. 10 wt. %), the balance of the composition being the aqueous carrying medium.

The suspension described above produces lasting pain relief in a body region by injection of the suspension around a nerve proximal to a body region where pain relief is desired. A typical injection may employ anywhere from 1 to 50 cc of the suspension (e.g. 5–30 cc).

Upon injection, the suspension releases the butyl aminobenzoate relatively slowly to give pain relief typically lasting several weeks or more. The butyl aminobenzoate is released sufficiently slowly to provide just enough anesthetic action to block pain sensation traveling through the nerves in the body region while leaving intact most other nerve conduction functions.

Successful results have been obtained injecting the composition in both dogs and humans. The composition employed in those uses was a suspension containing about 10 wt. % butyl aminobenzoate, prepared in the manner described below.

The following ingredients were added to a pyrex glass test tube:
  1 gram n-butyl-p-aminobenzoate;
  240 milligrams polyethylene glycol having a molecular weight of about 3600;
  10 cc sterile water;
  90 milligrams sodium chloride.

In the foregoing example, the polyethylene glycol suspending agent constitutes about 2.3% of the aqueous carrying medium based on the total weight of the suspending agent and water in the carrying medium. The sodium chloride was added to make an isotonic solution. The pH of the resulting mixture was adjusted to 4 by the addition of concentrated hydrochloric acid. The test tube was then capped and the contents thereof mixed thoroughly on a vortex mixer with a sterile glass mixing rod. As an alternative, the composition may be placed in a sealed vial and mixed with a magnetic stirrer. After mixing, the test tube and its contents were sterilized in a steam autoclave at 250° F. (121° C.) for ten minutes.

Butyl aminobenzoate is normally a solid at room temperature, but it melts during sterilization, and upon cooling following sterization, the butyl aminobenzoate precipitates as particles which have to be resuspended. This can be accomplished with a sterile glass mixing rod and a vortex mixer or using a magnetic stirrer with the composition in a sealed vial.

In animal tests, four dogs were each given epidural injections of the butyl aminobenzoate suspension as described above, each injection containing 3 cc of the suspension. The injections were made into the lumbar epidural space. Lumbar refers to the lower back area. The epidural space is the space inside the spinal canal that surrounds the dura matter, i.e. the outermost membrane that covers the spinal cord and the fluid that bathes the spinal cord.

All of the dogs were injected once a week. Two of the dogs were injected for five weeks and another two dogs were injected for ten weeks.

Each dog was sacrificed after its last injection, and the spinal cord was removed for histologic examination. No dogs showed any signs of neurological deficit (i.e. no loss of neurological function). Each time a dog was injected there was evidence of regional anesthesia persisting for a time varying between two hours and six hours. Regional anesthesia is the loss of sensation in the area of the body supplied (innervated) by the nerves originating in the area of the epidural injection.

None of the dogs suffered any ill effects either clinically, anatomically, or histologically. As a result of the dog tests, it was concluded that the composition was effective and safe.

The same butyl aminobenzoate suspension as described above was then used on nine human patients suffering from intractable pain, and the results of these human tests are summarized in the following table. Of the nine patients described in the table, the type of pain suffered was as follows: E. M. Suffered from incisional pain from an old thoracotomy (chest opening) incision; M. D. suffered from pain in the rib cartilages (costochondritis pain); and H. G. suffered from pain from post injection alcohol neuritis. All others suffered from cancer pain.

The numbers and letters in the second column of the table (e.g. $T_{12}$-$L_1$) define the area of the spine at which the injection was located. In all cases the suspension was injected around a nerve proximal to the body region where pain relief was desired. As used in the table, the term "block" refers to a nerve block obtained by injecting a local anesthetic.

| Patient | Location of Injection (block) | Quantity of 10% Suspension Injected | Result | Comments |
| --- | --- | --- | --- | --- |
| I. S. | Epidural block at $T_{12}$-$L_1$. | 16 cc | 50% pain relief after 1st block | |
| | Block repeated 6 days later at $L_{23}$ | 17 cc | Became essentially pain free & remained pain free for at least 2 months. | |
| C. J. | Epidural at $T_1$-$T_2$ | 30 cc | 90% pain relief. | Died after two weeks, pain free |
| A. C. | Epidural at $C_5$-$C_6$; | 15 cc | Complete pain relief at area innervated | |

-continued

| Patient | Location of Injection (block) | Quantity of 10% Suspension Injected | Result | Comments |
|---------|-------------------------------|-------------------------------------|--------|----------|
|  |  |  | by nerves undergoing treatment, for at least 2 months. |  |
|  | also, at the same time, 3rd division of the 5th cranial nerve. |  | Complete pain relief at area innervated by nerves undergoing treatment, for at least 2 months. |  |
|  | 20 days later right 9th cranial nerve | 6 cc | Complete pain relief at innervated area for at least 40 days |  |
| E. M. | Right 7th intercostal nerve | .5 cc | Complete pain relief for at least 10 months | Patient previously had been blocked several times with longest lasting local anesthetic previously available (Bupivacaine) with no lasting relief beyond a few hours |
| M. D. | Right 7th intercostal nerve | 4.5 cc | Complete pain relief for at least 8 months | Patient had had several previous blocks with Bupivacaine with no lasting relief |
| S. M. | Epidural $L_3$-$L_4$. | 15 cc | Complete pain relief for at least 5 months |  |
| M. R. | Epidural $T_1$-$T_2$. | 10 cc | Complete pain relief for 10 weeks | Patient expired from cancer at 10th week |
| C. A. | Epidural $L_4$-$L_5$. | 10 cc | Complete pain relief for 2 weeks | Patient died 2 weeks after block; had pain the last 24 hours in other areas not treated by block. |
| H. G. | Both right 8th & 9th intercostal nerves. | 10 cc each | Complete pain relief from both injections persisting for 2 weeks following which lost track of patient for follow-up purposes. |  |
|  | Epidural $T_8$-$T_9$. | 10 cc | Unable to evaluate extent of pain relief due to psychiatric problems with patient. |  |

As noted above, the composition and the aqueous carrying medium are substantially devoid of dextran which means that there is insufficient dextran present, if any, to interfere with the ability of the suspending agent (e.g. polyethylene glycol) to suspend the butyl aminobenzoate in the aqueous carrying medium.

The suspending agent is typically present in an amount up to about 10 wt. % based on the total weight of the suspending agent and water in the aqueous carrying medium. The minimum content of suspending agent should be at least the amount required to suspend whatever amount of butyl aminobenzoate is present in the composition, and this will vary with variations in the butyl aminobenzoate content. The maximum content of suspending agent is an amount, somewhat above the minimum amount described in the preceding sentence, and above which there will be an undesired effect on the composition or on the patient in whom the composition is injected; or, absent those effects, cost considerations will apply. Generally speaking, in a composition having a butyl aminobenzoate content of 5-15 wt.%, up to about 10 wt.% suspending agent (e.g. polyethylene glycol) in the aqueous carrying medium is sufficient.

The range of butyl aminobenzoate is determined by the minimum content required to produce the desired effect and by the maximum content above which there is no significant increase in the desired effect or at which undesired effects may occur. Typically, the butyl aminobenzoate is 5-15 wt. % of the composition.

The butyl aminobenzoate percentage may also depend upon the size of the dosage injected, and vice versa. The higher the concentration, the smaller the dosage required to inject a given amount of butyl aminobenzoate, and vice versa. Preferably, a composition containing about 10 wt. % butyl aminobenzoate is injected in dosages of 5 to 30 cc, 3-50 cc being a permissible range of dosages, for example.

A determination of the maximum and minimum content for the suspending agent and for the butyl aminobenzoate, in any given case, is within the skill of the art, given the information set forth above.

As noted above, polyethylene glycol is a preferred suspending agent, but other suspending agents may be used so long as they produce results comparable to those produced by polyethylene glycol and have no adverse effect on the basic and fundamental characteristics of the composition. Such a suspending agent should, of course, produce a stable, suspension of butyl aminobenzoate in the aqueous carrying medium and produce a slow release effect at the injection site. The suspending agent should have a relatively high molecular weight, greater than 1,000 (e.g. 1000-5000), and be non-toxic in the concentration required to perform the suspending function. Dextran should be excluded from the suspending agent and from the aqueous carrying medium, for reasons noted above.

A test for determining the suitability of a compound as a suspending agent for use in the present invention is to mix an aqueous medium containing up to 10 wt. % of the proposed suspending agent with 5-15 wt. % butyl aminobenzoate, in a glass test tube, and observe whether a stable suspension is formed. If what forms is an amorphous mass that settles out, or the like, as when dextran is used, then the proposed suspending agent is unsuitable.

The selection of suitable suspending agents other than polyethylene glycol should be within the skill of the art, given the information set forth above. Sodium carboxymethylcellulose and methylcellulose are other suitable candidates for use as suspending agents in a composition in accordance with the present invention, provided that dextran is excluded from the suspending agent and from the aqueous carrying medium, for the reasons noted above.

Butyl aminobenzoate is the preferred local anesthetic compound employed by the present invention because it is so highly insoluble in water. There are, as noted above, other local anesthetic compounds, highly insoluble in water. These other compounds are benzocaine (ethyl aminobenzoate), and orthoform. It is contemplated that at least benzocaine could be employed as the local anesthetic in a composition in accordance with the present invention. Except for the substitution of benzocaine for butyl aminobenzoate, the composition would otherwise be the same, including the exclusion of dextran which has the same adverse affect on the composition when it contains benzocaine as when it contains butyl aminobenzoate. As noted above, the inclusion of dextran in a composition otherwise in accordance with the present inventions produces an amorphous mass unsuitable for injection.

The foregoing detailed description has been given for clearness of understanding only, and no unnecessary limitations should be understood therefrom, as modifications will be obvious to those skilled in the art.

I claim:

1. A composition for producing lasting pain relief in a body region by injection, said composition consisting essentially of:
   a sterile, stable suspension of butyl aminobenzoate in a non-toxic, aqueous carrying medium in which said butyl aminobenzoate is insoluble;
   said butyl aminobenzoate constituting about 5 to 15 wt.% of said composition;
   said aqueous carrying medium consisting essentially of water as the major constituent and polyethylene glycol in an amount sufficient to maintain said butyl aminobenzoate in suspension;
   said suspension being substantially devoid of dextran.

2. A composition as recited in claim 1 wherein:
said polyethylene glycol is present in an amount up to about 10 wt. %, based on the total weight of the polyethylene glycol and water in said aqueous carrying medium.

3. A composition as recited in claim 1 wherein:
said carrying medium contains sodium chloride.

4. A composition as recited in claim 1 wherein:
said carrying medium is acidic.

5. A composition as recited in claim 4 wherein:
said carrying mdium has a pH in the range of about 3 to 5.

6. A composition as recited in claim 1 wherein:
said polyethylene glycol has a molecular weight less than about 5000.

7. A composition as recited in claim 1 wherein:
said suspension is capable, upon injection around a nerve proximal to a body region where pain relief is desired, of releasing said butyl aminobenzoate relatively slowly to give pain relief of at least several weeks duration.

8. A composition as recited in claim 7 wherein:
said suspension has a rate of release for the butyl aminobenzoate sufficiently slow to provide just enough anesthetic action to block pain sensations traveling through the nerves in said body region while leaving intact most other nerve conduction functions.

9. A composition for producing lasting pain relief in a body region by injection, said composition consisting essentially of:
   a sterile, stable suspension of butyl aminobenzoate in a non-toxic, aqueous carrying medium in which said butyl aminobenzoate is insoluble;
   said suspension agent consisting essentially of water as the major constituent and polyethylene glycol;
   said polyethylene glycol being present in an amount up to about 10 wt.%, based on the total weight of the polyethylene glycol and water in said aqueous carrying medium;
   said suspension being substantially devoid of dextran.

10. A composition for producing lasting pain relief in a body region by injection, said composition consisting essentially of:
    a sterile, stable suspension of butyl aminobenzoate in a non-toxic, aqueous carrying medium in which said butyl aminobenzoate is insoluble;
    said butyl aminobenzoate constituting about 5 to 15 wt.% of said suspension, with the balance being said aqueous carrying medium;
    said aqueous carrying medium consisting essentially of water as the major constituent and a suspending agent for said butyl aminobenzoate, said suspending agent being present in an amount sufficient to maintain said butyl aminobenzoate in suspension;
    said suspension being substantially devoid of dextran.

11. A method for producing lasting pain relief in a body region by injection, said method comprising the step of:
    injecting, around a nerve proximal to the body region where pain relief is desired, a sterile, stable suspension of butyl aminobenzoate in an aqueous, non-toxic carrying medium in which said butyl aminobenzoate is insoluble, said suspension being substantially devoid of dextran;
    said butyl aminobenzoate constituting about 5 to 15 wt.% of said composition;
    said aqueous carrying medium consisting essentially of water as the major constituent and polyethylene glycol in an amount sufficient to maintain said butyl aminobenzoate in suspension.

12. A method as recited in claim 11 wherein said injecting step comprises:
injecting 1-50 cc of said suspension.

13. A method as recited in claim 12 wherein said injecting step comprises:
    injecting about 5–30 cc of said suspension.

14. A method as recited in claim 15 wherein:
    said polyethylene glycol is present in an amount up to about 10 wt. %, based on the total weight of the polyethylene glycol and water in said aqueous carrying medium.

15. A method as recited in claim 11 wherein:
    said carrying medium contains sodium chloride.

16. A method as recited in claim 11 wherein:
    said carrying medium is acidic.

17. A method as recited in claim 16 wherein:
    said carrying medium has a pH in the range of about 3 to 5.

18. A method as recited in claim 11 wherein:
    said polyethylene glycol has a molecular weight less than about 5000.

19. A method as recited in claim 11 wherein:
    said suspension, upon injection, releases said butyl aminobenzoate relatively slowly to give pain relief of at least several weeks duration.

20. A method as recited in claim 19 wherein:
    said suspension releases said butyl aminobenzoate sufficiently slowly to provide just enough anesthetic action to block pain sensation traveling through the nerves in said body region while leaving intact most other nerve conduction functions.

21. A method for producing lasting pain relief in a body region by injection, said method comprising the step of:
    injecting, around a nerve proximal to the body region where pain relief is desired, a sterile, stable suspension of butyl aminobenzoate in an aqueous, nontoxic carrying medium in which said butyl aminobenzoate is insoluble, said suspension being substantially devoid of dextran;
    said suspension agent consisting essentially of water as the major constituent and polyethylene glycol;
    said polyethylene glycol being present in an amount up to about 10 wt.%, based on the total weight of the polyethylene glycol and water in said aqueous carrying medium.

22. A method for producing lasting pain relief in a body region by injection, said method comprising the step of:
    injecting, around a nerve proximal to the body region where pain relief is desired, a sterile, stable suspension of butyl aminobenzoate in an aqueous, nontoxic carrying medium in which said butyl aminobenzoate is insoluble, said suspension being substantially devoid of dextran;
    said butyl aminobenzoate constituting about 5 to 15 wt.% of said suspension, with the balance being said aqueous carrying medium;
    said aqueous carrying medium consisting essentially of water as the major constituent and a suspending agent for said butyl aminobenzoate, said suspending agent being present in an amount sufficient to maintain said butyl aminobenzoate in suspension.

* * * * *